United States Patent [19]

Gillier et al.

[11] Patent Number: 4,492,116

[45] Date of Patent: Jan. 8, 1985

[54] APPARATUS FOR THE OPTICAL OBSERVATION OF PHENOMENA IN MIXTURES

[75] Inventors: Hugues Gillier, Paris; Jean-Claude Redasse, Noisy-le-Sec; Maurice Renaut, Aulnay sous Bois, all of France

[73] Assignee: Commissariat a l'Energie Atomique, Paris, France

[21] Appl. No.: 507,089

[22] Filed: Jun. 23, 1983

[30] Foreign Application Priority Data

Jun. 23, 1982 [FR] France ............................. 82 10974

[51] Int. Cl.³ ........................................... G01N 21/00
[52] U.S. Cl. ................................. 73/432 R; 73/53; 356/440
[58] Field of Search .................. 356/389, 437, 440; 73/53, 432 R, 432 Z

[56] References Cited

PUBLICATIONS

Journal of Applied Physics, vol. 52, No. 2, Feb. 1981, American Institute of Physics, New York (US), L. Baker et al., "Heuristic Mode of the Non-Linear Rayleigh-Taylor Instability", pp. 655-663, 665-666.

Review of Scientific Instruments, vol. 48, No. 4, Apr. 1977, American Institute of Physics, New York (US), W. Black et al., "Interferometric Method for the Determination of Binary Gas Mass Diffusivities", pp. 476-481.

Soviet Physics JETP, vol. 44, No. 2, Aug. 1976, American Institute of Physics, New York (US), V. Andronov et al., "Turbulent Mixing at Contact Surface Accelerated by Shock Waves", pp. 424-427.

Primary Examiner—Stephen A. Kreitman
Assistant Examiner—Hezron Williams
Attorney, Agent, or Firm—Dennis P. Clarke

[57] ABSTRACT

Apparatus for the optical observation of the evolution of instabilities between two fluids having different densities subject to high initial pressures, of the type comprising an observation chamber with parallel faces containing the two fluids, initially separated by a diaphragm, and wherein it comprises in combination the arrangement of the observation chamber within a tight enclosure equipped with static pressurizing means and whereof one face is constituted by an optical observation window parallel to the two parallel faces of the observation chamber, the diaphragm having a straight cylindrical shape and is coupled to a mechanical extraction shaft, the geometrical axes of the diaphragm and the extraction shaft being perpendicular to the faces of the observation chamber, the extraction shaft sealingly sliding through the wall of the enclosure opposite to the said window, while part of the extraction shaft external of the pressure enclosure is integral respectively with a piston sliding within a cylinder and which can be actuated by a high pressure fluid in order to drive the extraction shaft towards the outside of the enclosure, a mechanical device for locking and unlocking the extraction shaft and device for stopping the extraction shaft at the end of its travel.

4 Claims, 2 Drawing Figures

APPARATUS FOR THE OPTICAL OBSERVATION OF PHENOMENA IN MIXTURES

BACKGROUND OF THE INVENTION

The present invention relates to the field of fluid physics and more particularly to the study by optical observation of the evolution of instabilities occurring at the separating interface between two fluids of different densities subject to a non-zero acceleration.

Hitherto, this study, called Taylor instabilities, has always remained limited to the case where the two fluids are exposed to the acceleration of the earth's gravitational field and utilizes simple equipment essentially comprising an observation chamber having parallel faces containing the two fluids, initially separated by a generally sinusoidal diaphragm, which a simple device extracts at the start of the experiment in order to bring into contact with one another the two fluids of different densities.

SUMMARY OF THE INVENTION

The present invention aims at extending the scope of this study to much wider experimental conditions and in particular under accelerations well above those of the natural gravitational field. These accelerations are obtained by the application to one of the fluids of a high pressure, which can reach several dozen bars.

The more specific aim of the invention is to solve the problem, which then becomes critical, of the extraction in a minimum possible time of the diaphragm which, before the start of the experiment, separates the two fluids under high pressure.

Thus, the present invention relates to an apparatus for the optical observation of the evolution of instabilities between two fluids having different densities subject to high initial pressures, of the type comprising an observation chamber with parallel faces containing the two fluids, initially separated by a diaphragm, and wherein it comprises in combination the arrangement of the observation chamber within a tight enclosure equipped with static pressurizing means and whereof one face is constituted by an optical observation window parallel to the two parallel faces of the observation chamber, the diaphragm having a straight cylindrical shape and is coupled to a mechanical extraction shaft, the geometrical axes of the diaphragm and the extraction shaft being perpendicular to the faces of the observation chamber, the extraction shaft sealingly sliding through the wall of the enclosure opposite to the said window, whilst part of the extraction shaft external of the pressure enclosure is integral respectively with a piston sliding within a cylinder and which can be actuated by a high pressure fluid in order to drive the extraction shaft towards the outside of the enclosure, a mechanical device for locking and unlocking the extraction shaft and a device for stopping the extraction shaft at the end of its travel.

When using this apparatus, the diaphragm separating the two fluids is initially fitted. The extraction shaft, which is fixed to the diaphragm, is then locked. The lower part of the observation chamber is then filled with a first fluid and gas pockets which may still exist beneath the diaphragm are eliminated. The upper part of the observation chamber is then filled with a second fluid having a different density to the first fluid. The enclosure containing this chamber is then progressively pressurized by introducing a gaseous fluid until the desired pressure is reached. In the same way, the high pressure fluid is introduced into a cylinder containing the aforementioned piston and which is integral with the extraction shaft. When the selected high pressure, which can differ from that of the enclosure, is reached in the cylinder, the shaft unlocking device is actuated. The extraction shaft is then released and is propelled with a very high force in order to extract the diaphragm. When the diaphragm has been completely removed from the observation chamber, the end-of-travel stopping device acts in order to stop the mechanical extraction shaft.

The above description shows the advantages provided by the apparatus according to the invention, whose characteristic organisation makes it possible to separate in an optimum manner the different functions to be performed.

Firstly, the tight autonomous static over-pressure enclosure containing the observation chamber can be dimensioned and equipped in such a way that it makes it possible to produce overpressure values, which are as high as desired in order to extend the experimental field.

Secondly, the driving force of the mechanical shaft for retracting the diaphragm can be as high as necessary by choosing as a consequence thereof the surface of the piston fixed to said shaft and the high pressure value of the fluid actuating it. Thus, it is possible to reduce to a minimum acceptable value the diaphragm extraction time.

Another object of the invention is to permit the automatic starting and performance of a certain number of functions on the basis of an initial time reference correlated with the start of an experiment, i.e. the extraction of the diaphragm.

To this end, the invention relates to an apparatus of the aforementioned type, wherein part of the extraction shaft is fixed to a plate, which has calibrated slots with known spacings, and which can move between a radiation source and a radiation receiver in order to produce a pulse train constituting an image of the diaphragm displacement.

The first pulse of the aforementioned train can in particular control the automatic starting of a film marking device, the photographic camera having previously been operated, the shooting speed being designated by a time base permanently inscribed on the film.

A further object of the invention is to make it possible to vary the conditions of the instabilities caused.

Thus, the invention relates to an apparatus of the aforementioned type, wherein the lower part of the observation chamber is connected by a pipe to an expansion vessel having regulatable damping.

BRIEF DESCRIPTION OF THE DRAWINGS

The invention is described in greater detail hereinafter relative to non-limitative embodiments and with reference to the attached drawings, wherein show.

DETAILED DESCRIPTION OF THE INVENTION

Figure 1:
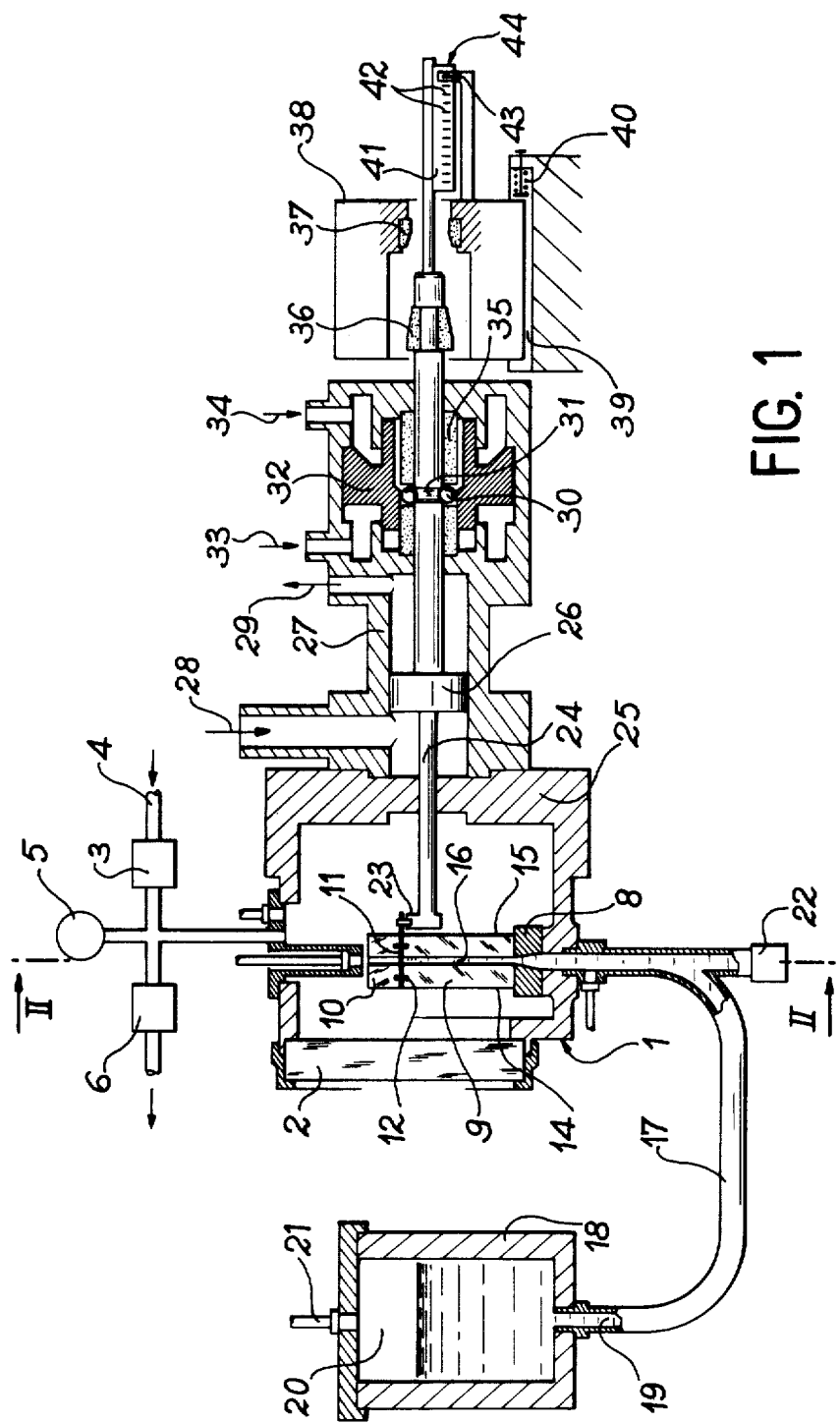
FIG. 1 a diagrammatic axial longitudinal sectional view of the apparatus according to the invention.

The apparatus comprises a first part constituted by the static overpressure enclosure. The latter is formed by a circular cylindrical chamber 1, whereof one front face is closed by an observation window 2, made from thick glass or a plastic material, such as that known under the trade name Plexiglass.

The interior of the enclosure is connected by a feed valve 3 to a high pressure fluid source 4, e.g. compressed air which can be at experimental pressures of 20, 40, 60 and even 100 bars. A pressure gauge 5 indicates the pressure of this high pressure fluid source. Following the experiment, the enclosure is decompressed by opening an exhaust valve 6. Different pressure sensors 7 are provided to measure, at different locations, the pressures during the experiment and permit their recording.

The actual observation chamber is located within enclosure 1. This chamber, supported by a base 8, is formed by a lower block 9 and an upper block 10 positioned just above it, with the interposing of diaphragm 11. The seal between blocks 9 and 10 is ensured by the presence of diaphragm 11 and by O-ring seals 12. Following the fitting of diaphragm 11, the assembly of blocks 9 and 10 is maintained in place with the aid of posts 13.

In the represented embodiment, when viewed in section, the diaphragm is shaped like a circular arc. The geometrical axis of the cylinder formed by it is perpendicular to the two parallel faces 14, 15 of the observation chamber. It is obvious that the sectional shape of the diaphragm could differ and can be planar, sinusoidal, or the like.

Figure 2:
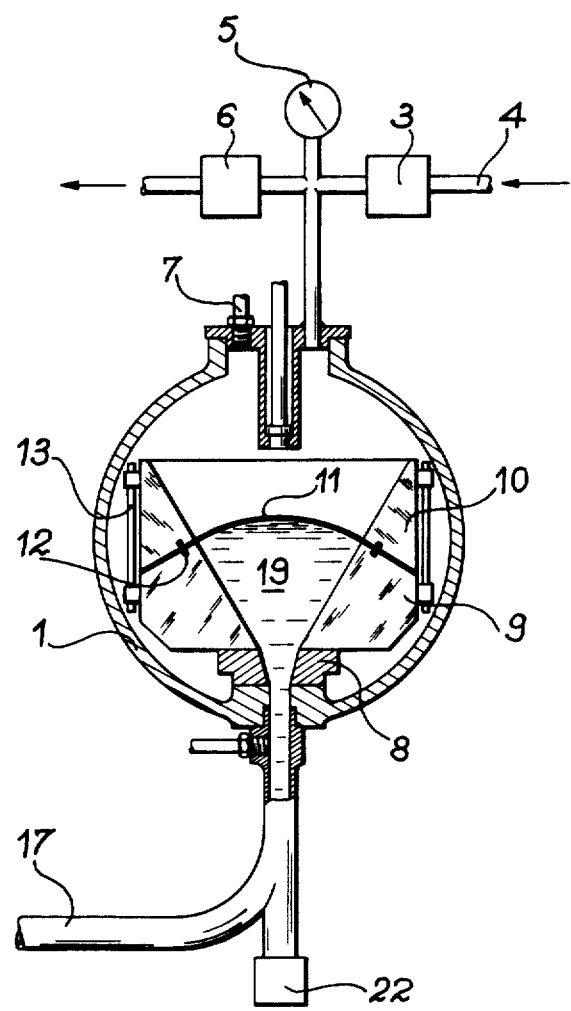
FIG. 2 a diagrammatic sectional view through II—II of the apparatus of FIG. 1.

In the present embodiment, the internal useful volume 16 of the observation chamber, cf FIG. 2, converges towards the bottom and is connected to the correspondingly shaped inlet in base 8. In the same way, the shape of this internal useful volume 16 could differ. The lower part of volume 16 communicates by a pipe 17 with an expansion vessel 18.

The fluid 19, e.g. the lighter fluid, occupies the entire volume within the observation chamber, located beneath diaphragm 11 and passes through pipe 17 to expansion vessel 18, where it is surmounted by a gas gap, e.g. an air gap 20 which, during the experiment, exerts a breaking force on the fluid flow and which is regulatable by the initial thickness of the gas gap. A sensor 21 measures the pressure of gas gap 20.

According to another feature of the invention, a bubble trapping device 22 is provided below the lower block 9 of the observation chamber. This trap makes it possible to extract the gas bubbles, which, after filling the light liquid, adhere to the diaphragm 11 in the upper part of the lower chamber. This trap is constituted by an orifice sealed by an elastic material plug. Via the plug, this orifice permits the introduction of one of the ends of a metal capillary tube until it is level with the bubble. The latter is sucked in via the other end of the capillary tube by means of a rubber bulb. The capillary tube is then removed and a metal plug seals the orifice during the experiments. Diaphragm 11 is connected, by a coupling 23, to a mechanical shaft 24 for extracting the diaphragm. Shaft 24 sealingly slides in the front wall 25 of the overpressure enclosure 1.

In combination with the first part described hereinbefore, the apparatus has a second part constituting the control system for the displacement of the diaphragm extraction shaft 24.

This system firstly comprises the drive means for shaft 24, which is constituted by a piston 26 fixed to the latter and able to slide within a cylinder 27, equipped with a pipe 28 for feeding in a high pressure fluid, e.g. air, as well as an exhaust pipe 29. This system also has a device for locking/unlocking the shaft 24 in the axial position.

In the described embodiment, said member is constructed in the following way. Balls 30 are located in a groove 31 made in shaft 24. In the locked position, said balls 30 are engaged in groove 31 under the action of a piston 32 having an inner bore, on its part shown to the left in the drawing, which precisely maintains the balls 30 in groove 31. The thus represented position of piston 32 is obtained by the action of a pressurized fluid introduced by a pipe 33. After fitting the piston, the fluid intake is interrupted.

Unlocking is obtained by introducing a fluid into the unlocking pipe 34. Piston 32 then moves to the left and a wider bore 35 is positioned facing balls 30, which then leave the groove 31 and release the extraction shaft 24.

The system controlling the displacement of extraction shaft 24 finally comprises a device for stopping shaft 24 at the end of its travel. In the present case, this device comprises a consumable male cone 36, which is made from a material which deforms whilst consuming energy, e.g. aluminium and which is fitted into a female cone 37 and is crushed at the end of travel. In order not to disturb the experiment taking place as a result of impacts, it is possible to mechanically insulate the support of female cone 37 from the remainder of the apparatus. For example, support 38 is mounted on slides 39 with damping springs 40.

Finally, the apparatus comprises, according to another advantageous feature of the invention, a member for measuring the displacement and speed of the diaphragm extraction shaft 24.

This member is very simply constituted by a blade or plate 41, integral with shaft 24 and having calibrated slots 42, which are spaced from one another by a known value. A radiation source 43, e.g. a light-emitting diode, is placed on one side of plate 41, whilst a receiver 44 of said radiation, e.g. a phototransistor, is placed on the other side of the plate. During the displacement of shaft 24 and therefore plate 41, all these means supply appropriate known electronics, which produces a pulse train.

The operating mode of the aforementioned apparatus has become readily apparent as a result of the above description.

It is merely pointed out that, at the start of an experiment, the diaphragm is flush or is slightly set back from the front face of the observation chamber. This initial condition ensures that when the left-hand edge of the diaphragm arrives at the inlet of the inner useful volume 16 of the chamber, extraction shaft 24 has had the time to reach its maximum speed in order to reduce to the minimum the real time for extracting the diaphragm from the useful volume 16.

It is pointed out that for pressures of 40 bars exerted in extraction cylinder 27, diaphragm extraction speeds of 20 mm/ms have been obtained. With a width of the useful internal volume 16 of the observation chamber of 1 (FIG. 1) with a value of 7 mm, a passage time of approximately 0.34 ms is required for extracting the diaphragm from useful volume 16.

The invention is not restricted to the embodiment described hereinbefore.

What is claimed is:

1. An apparatus for the optical observation of the evolution of instabilities between two fluids having different densities subject to high initial pressures, of the type comprising an observation chamber with parallel faces containing the two fluids, initially separated by a diaphragm, and wherein it comprises in combination the arrangement of the observation chamber within a tight enclosure equipped with static pressurizing means and whereof one face is constituted by an optical observation window parallel to the two parallel faces of the observation chamber, the diaphragm having a straight cylindrical shape and is coupled to a mechanical extraction shaft, the geometrical axes of the diaphragm and the extraction shaft being perpendicular to the faces of the observation chamber, the extraction shaft sealingly sliding through the wall of the enclosure opposite to the said window, whilst part of the extraction shaft external of the pressure enclosure is integral respectively with a piston sliding within a cylinder and which can be actuated by a high pressure fluid in order to drive the extraction shaft towards the outside of the enclosure, a mechanical device for locking and unlocking the extraction shaft and a device for stopping the extraction shaft at the end of its travel.

2. An apparatus according to claim 1, wherein the device for stopping the diaphragm extraction shaft at the end of its travel comprises a cone, made from a material able to deform whilst consuming high energy levels, which is keyed to the shaft and which at the end of the travel is fitted into a female cone.

3. An apparatus according to claim 1, wherein part of the extraction shaft is fixed to a plate, which has calibrated slots with known spacings, and which can move between a radiation source and a radiation receiver in order to produce a pulse train constituting an image of the diaphragm displacement.

4. An apparatus according to claim 1, wherein the lower part of the observation chamber is connected by a pipe to an expansion vessel having regulatable damping.

* * * * *